(12) United States Patent
Zhu et al.

(10) Patent No.: US 12,016,244 B1
(45) Date of Patent: Jun. 18, 2024

(54) ASYMMETRIC ORGANIC PHOTOVOLTAIC ACCEPTOR MATERIAL IN AN A-D-D'-A TYPE AND USE

(71) Applicant: CHANGZHOU UNIVERSITY, Jiangsu (CN)

(72) Inventors: Weiguo Zhu, Changzhou (CN); Jianing Zhu, Changzhou (CN); Hua Tan, Changzhou (CN); Mengbing Zhu, Changzhou (CN); Rulin Hao, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 18/418,330

(22) Filed: Jan. 21, 2024

Related U.S. Application Data

(63) Continuation-in-part of application No. PCT/CN2022/096517, filed on Jun. 1, 2022.

(30) Foreign Application Priority Data

Jul. 21, 2021 (CN) .......................... 202110823145.1

(51) Int. Cl.
*H10K 85/60* (2023.01)
*C07D 495/04* (2006.01)
*H10K 30/30* (2023.01)
*H10K 30/50* (2023.01)

(52) U.S. Cl.
CPC ....... *H10K 85/6576* (2023.02); *C07D 495/04* (2013.01); *H10K 85/626* (2023.02); *H10K 30/30* (2023.02); *H10K 30/50* (2023.02)

(58) Field of Classification Search
CPC ................................................ H10C 85/6576
See application file for complete search history.

(56) References Cited

U.S. PATENT DOCUMENTS

2021/0367159 A1\* 11/2021 Mitchell .............. H10K 85/657
2022/0140266 A1\* 5/2022 Smith .................... H10K 85/40
136/256

FOREIGN PATENT DOCUMENTS

CN 109081825 A 12/2018
CN 110218216 A 9/2019
(Continued)

OTHER PUBLICATIONS

First Office Action in Chinese Application No. 202110823145.1 mailed on Mar. 31, 2022, 9 pages.
(Continued)

*Primary Examiner* — William D Young
(74) *Attorney, Agent, or Firm* — Porus IP LLC (57) ABSTRACT

An asymmetric organic photovoltaic acceptor material in an A-D-D'-A type is provided. A backbone containing noncovalent conformational lock is co-constructed with alkoxy-indenothiophene and cyclopentadithiophene two-electron donor (D-D') unit, and the ends are modified with fluorine- and chlorine-atom-substituted 3-(dicyanomethylidene)inden-1-one. The acceptor containing only a simple condensed ring has multiple advantages such as a coplanar backbone, low energy disorder, and J-aggregation tendency, and this type of asymmetric small-molecule acceptor has a controllably adjustable optical bandgap in the range of 1.30-1.45 eV, which is capable of combining with most donor materials to construct highly efficient binary bulk heterojunction organic solar cell. When the donor material is polymer PM6, the photoelectric conversion efficiency of the binary organic solar cells (OSCs) device is as high as 13.67%, with an open-circuit voltage ($V_{oc}$) of 0.85 eV and energy loss ($E_{loss}$) is only 0.50 V.

6 Claims, 4 Drawing Sheets

(56) References Cited

FOREIGN PATENT DOCUMENTS

CN 111039961 A 4/2020
CN 113563362 A 10/2021

OTHER PUBLICATIONS

Notification to Grant Patent Right for Invention in Chinese Application No. 202110823145.1 mailed on May 10, 2022, 4 pages.

Tan, Hua et al., An A-D-D-A-type non-fullerene small-molecule acceptor with strong near-infrared absorption for high performance polymer solar cells, J. Mater. Chem. C, 2019, 6 pages.

International Search Report in PCT/CN2022/096517 mailed on Aug. 9, 2022, 7 pages.

Written Opinion in PCT/CN2022/096517 mailed on Aug. 9, 2022, 8 pages.

Zhu, Jianing et al., Non-Fused-Ring Asymmetrical Electron Acceptors Assembled by Multi-Functional Alkoxy Indenothiophene Unit to Construct Efficient Organic Solar Cells, Chemical Engineering Journal, 444: 1-6, 2022.

Chen, Shanshan et al., Ultrafast Channel II Process Induced by a 3-D Texture with Enhanced Acceptor Order Ranges for High-Performance Non-Fullerene Polymer Solar Cells, Energy Environ. Sci., 11(9): 2569-2580, 2018.

Kang, Zhenjing et al., Push-Pull Type Non-Fullerene Acceptors for Polymer Solar Cells: Effect of the Donor Core, ACS Appl. Mater. Interfaces, 9(29): 24771-24777, 2017.

\* cited by examiner

ASYMMETRIC ORGANIC PHOTOVOLTAIC ACCEPTOR MATERIAL IN AN A-D-D'-A TYPE AND USE

CROSS-REFERENCE TO RELATED APPLICATIONS

This application is a continuation-in-part of an international application No. PCT/CN2022/096517, filed on Jun. 1, 2022, which claims priority to Chinese Patent Application No. 202110823145.1, filed on Jul. 21, 2021, the contents of which are hereby incorporated by reference to its entirety.

TECHNICAL FIELD

The present disclosure relates to the field of organic photovoltaic technology, and in particular to a structurally simple, asymmetric organic photovoltaic acceptor material in an A-D-D'-A type, and the use there of in an organic solar cell.

BACKGROUND

The development of simple condensed ring small-molecule acceptor materials (simple condensed ring means a count of condensed rings ≤3) in an organic solar cell obviously lags behind large condensed ring small-molecule acceptor materials (large condensed ring means a count of condensed rings >3). Most of such materials have been reported as acceptor-donor-core-donor-acceptor (A-D-C-D-A) type small molecules with symmetric structures, wherein the D unit is mainly dithienocyclopentadiene (DTC). To date, the photovoltaic efficiencies of binary solar cell devices prepared based on this type of acceptor material blended with polymer donors such as poly([2,6'-4,8-bis-((2-ethylhexyl)-thiophen-5-yl)benzo[1,2-b;3,3-b]dithiophene]-alt-[1,3-bis-(thiophen-5-yl)-5,7-bis-(2-ethylhexyl)benzo[1,2-c:4,5-c']dithiophene-4,8-dione])(PBDB-T), poly[(2,6-(4,8-bis(5-(2-ethylhexyl-3-fluoro)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione)] (PM6), or poly[[5,6-difluoro-2-(2-hexyldecyl)-2H-benzotriazole-4,7-diyl]-2,5-thiophenediyl[4,8-bis[5-(2-ethylhexyl)-2-thienyl]benzo[1,2-b:4,5-b']dithiophene-2,6-diyl]-2,5-thiophenediyl] (J52) are typically 10-14%. However, compounds containing DTC units are costly, have poorer photostability, and the presence of a central nucleus (a C unit linked by a carbon-carbon single bond) tends to adversely affect the photovoltaic performance of the solar cells (e.g., resulting in H-aggregation and reduced electron mobility).

Indenothiophene has coplanarity and good stability, and the utilization of asymmetric indeno thiophene structural units to construct efficient and structurally simple condensed ring small molecule acceptor materials is an important topic in the frontier research of small molecule acceptor materials.

SUMMARY

In view of the critical issues of low photovoltaic conversion efficiency and large energy loss ($E_{loss}$) in current structurally simple small molecule photovoltaic acceptor materials, the present disclosure provides a structurally simple of an asymmetric organic photovoltaic acceptor material in an A-D-D'-A type.

Embodiments of the present disclosure synthesizes a structurally simple asymmetric A-D-D'-A type organic photovoltaic acceptor material with a narrow bandgap using a noncovalent conformational lock strategy for the planar molecule design. This type of small-molecule acceptor material is designed by introducing an alkoxy group onto the benzene ring of indenothiophene, which then forms a noncovalent conformational lock with the thiophene ring of dithienocyclopentadiene (DTC). This ensures the solubility of the material while allowing for energy level and band gap fine-tuning, and promotes its cold crystallization, thereby modulating the material's photophysical, electrochemical, and aggregation behaviors, and ultimately improving the performance of the photovoltaic device. Due to the wide range of sources of benzene ring derivatives, a variety of functional groups may be introduced simultaneously.

Therefore, this type of asymmetric A-D-D'-A-type organic photovoltaic acceptor materials is of great significance for the development of low-cost and high-efficiency organic solar cells.

Embodiments of the present disclosure provide the asymmetric organic photovoltaic acceptor material in the A-D-D'-A type has a structure represented by Formula 1:

(Formula 1)

wherein $R^1$, $R^2$, and $R^3$ are linear or branched $C_{1-20}$ alkyl; X is an H, F, or Cl atom.

In some embodiments, the asymmetric organic photovoltaic acceptor material in the A-D-D'-A type has a structure represented by Formula 2:

(Formula 2)

R = -CH₃, X = F, SM1
R = -CH₃, X = Cl, SM2
R = 2-ethylhexyl, X = F, SM3
R = 2-ethylhexyl, X = Cl, SM4

One of the embodiments of the present disclosure provides a use of the asymmetric organic photovoltaic acceptor material in the A-D-D'-A type, the asymmetric organic photovoltaic acceptor material is applied to a photoactive layer of the organic solar cell.

The present disclosure provides the photovoltaic acceptor material as the A-D-D'-A-type small molecule containing only a simple condensed ring unit has the following characteristics: (1) compared to structurally complex large condensed ring small molecule acceptors, the molecular structure is greatly simplified; (2) the asymmetric D-D' units maintain the coplanarity of the molecular backbone through noncovalent conformational lock; (3) compared with the A-D-C-D-A type symmetric small-molecule acceptor, the main advantage lies in the reduction of the C-C single bond between the units, which is conducive to the expansion of the range of π-electron delocalization; and (4) asymmetric structure has a certain advantage in the donor/acceptor energy level matching, making it easier to achieve a balance between the open-circuit voltage and the short-circuit current; (5) this type of small molecule acceptor also has the characteristics of simple synthesis and structural diversity.

BRIEF DESCRIPTION OF THE DRAWINGS

The present disclosure is further illustrating by way of exemplary embodiments, which is describing in detail with reference to the accompanying drawings. These embodiments are not limiting, and in these embodiments, the same numbering denotes the same structure, wherein.

DETAILED DESCRIPTION

In order to more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for a person of ordinary skill in the art to apply the present disclosure to other similar scenarios in accordance with these drawings without creative labor. The present disclosure can be applied to other similar scenarios based on these drawings without creative labor. Unless obviously obtained from the context or the context illustrates otherwise, the same numeral in the drawings refers to the same structure or operation.

As shown in the present disclosure and in the claims, unless the context clearly suggests an exception, the words "a", "one", "an" and/or "the" do not refer specifically to the singular form but may also include the plural form. Generally, the terms "includes", "include", "including", "comprise", "comprises", and "comprising" only suggest the inclusion of explicitly identified steps and elements that do not constitute an exclusive list, and the method or apparatus may also include other steps or elements.

Some commonly used abbreviations and English words in this present disclosure have the following meanings:
OSCs: Organic solar cells.
PCE: Power Conversion Efficiency.
$V_{oc}$: Open-circuit Voltage.
$E_{loss}$: Energy loss.
$E_g$: Band gap.
$E_{ox}$: Oxidation potential.
$E_{red}$: Reduction potential.
$J_{sc}$: Short-circuit Current Density.
$E_{HOMO}$: energy level of the Highest Occupied Molecular Orbital.
$E_{LUMO}$: energy level of the Lowest Unoccupied Molecular Orbital.

FF: Fill Factor.

EQE: External Quantum Efficiency.

PBDB-T: CAS:1415929-80-4. Poly([2,6'-4,8-bis-((2-ethylhexyl)-thiophen-5-yl)benzo[1,2-b;3,3-b]dithiophene]-alt-[1,3-bis-(thiophen-5-yl)-5,7-bis-(2-ethylhexyl)benzo[1,2-c:4,5-c']dithiophene-4,8-dione]).

PM6: CAS: 1802013-83-7. Poly[(2,6-(4,8-bis(5-(2-ethylhexyl-3-fluoro)thiophen-2-yl)-benzo[1,2-B:4,5-B']dithiophene])-alt-(5,5-(1',3'-di-2-thiophene-5',7'-bis(2-ethylhexyl)benzo[1',2'-C:4',5'-C']dithiophene-4,8-dione).

J52: 1887136-01-7. Poly[[5,6-difluoro-2-(2-hexyldecyl)-2H-benzotriazole-4,7-diyl]-2,5-thiophenediyl[4,8-bis[5-(2-ethylhexyl)-2-thienyl]benzo[1,2-b:4,5-b']dithiophene-2,6-diyl]-2,5-thiophenediyl].

The following are definitions of some of the terms used in the present disclosure.

As used herein, "photovoltaic efficiency" (which may also be referred to as "photovoltaic conversion efficiency" or "power conversion efficiency") refers to the efficiency with which a solar cell converts light energy into heat energy.

As used herein, "external quantum efficiency", is the ratio of the number of electrons produced from the solar cell per unit time to the number of photons irradiated on the surface of the solar cell per unit time ratio.

As used herein, "A-D-D'-A type" organic photovoltaic acceptor materials refer to a class of materials that contain both electron donors (D is the abbreviation of donor) and electron acceptors (A is the abbreviation of acceptor). The optical bandgap is able to readily tuned by the electronic structure of D and A. Wherein, the "D-D'" unit represents two asymmetric donor structures.

As used herein, the "C" unit in "A-D-C-D-A type" represents a nuclear structure connected by a carbon-carbon single bond. In the "A-D-C-D-A" molecule, the D and A on either side of the nuclear structure are centered on the "C" unit and are symmetrically distributed.

As used herein, the term "J-V curve" refers to the current density-voltage curve of a solar cell device tested under illumination conditions, which involves important output characteristic parameters, including $V_{oc}$, $J_{sc}$, FF, and PCE, for evaluating solar cell performance.

As used herein, the term "EQE curve" refers to the external quantum efficiency curve of a solar cell device tested at a specific wavelength. The EQE value represents the ratio of the number of electrons collected to the number of photons absorbed (the ability of an incident photon to be converted to an electron) at a specific wavelength, and is used to assess the current efficiency performance of a solar cell.

As used herein, the term "$E_{loss}$" refers to the amount of energy that is lost during the conversion of light energy into electrical energy in a solar cell.

One of the embodiments of the present disclosure provides the asymmetric organic photovoltaic acceptor material in the A-D-D'-A-type, wherein A in the A-D-D'-A structure represents the acceptor and D represents the donor, and the acceptor material has a structure represented by Formula 1:

(Formula 1)

wherein, $R^1$, $R^2$, $R^3$ are linear or branched $C_1$-$C_{20}$ alkyl; and X is an H, F, or Cl atom.

The organic photovoltaic acceptor material is a material used in organic solar cells, primarily for absorbing light energy and converting it into electricity. These materials are usually organic molecules or polymers that have good photovoltaic properties and are capable of generating electric current under light conditions. The design and selection of the organic photovoltaic acceptor materials are critical for improving the efficiency of solar cells. These materials are often molecularly engineered or synthesized to modulate their optical, electrical, and structural properties to achieve higher photovoltaic conversion efficiency.

The "asymmetry" of the organic photovoltaic acceptor material refers to an asymmetric structure of the D-D' unit formed by noncovalent conformational lock of non-covalent bonds, thereby the overall structure of the A-D-D'-A type organic photovoltaic acceptor material is asymmetric. The noncovalent conformational lock refers to the portion of the noncovalent bonding forces present between the molecules.

Molecules with a coplanar conformation favor the delocalization of electrons, as well as contributing to the formation of tighter molecular stacks, which are conducive to charge jumps. In order to improve the coplanarity of the conjugated system and avoid the free rotation of the neighboring aromatic rings connected by single bonds, it is important to connect the neighboring aromatic rings by covalent bonding with C, Si, or N atoms to form a condensed ring structure that has a higher rigidity and better planarity. This has become the key to prepare organic photovoltaic acceptor materials. The rotation of the single bond is prevented by non-bonding forces, but this method is usually difficult in synthesis and increases the cost of the material. It is possible to improve the coplanarity of conjugated molecules by introducing a structure of non-covalent "conformational locks" into the molecule. The introduction of noncovalent bonding forces, as opposed to covalent bonding forces, avoids the need for complex synthesis routes, improves the coplanarity of the conjugated material and increases the carrier mobility, so as to result in a substantial improvement in the performance of the associated optoelectronic devices.

In some embodiments, the D and D' in the D-D' unit of the asymmetric organic photovoltaic acceptor material in the A-D-D'-A type are an alkoxyindenothiophene and cyclopentadieno-dithiophene, and the A unit is a fluorine or chlorine atom-substituted 3-(dicyanomethylidene)inden-1-one.

In some embodiments, alkoxyindenothiophene may be made from 2-bromo-4-methoxybenzoic acid by a classical reaction such as esterification, suzuki coupling, Foucault acylation, and Wong-Ming-Lung reduction.

One of the embodiments of the present disclosure provides the asymmetric organic photovoltaic acceptor material in the A-D-D'-A type, which also has the structure shown in the following Formula 2:

suitable solvent and ensuring adequate mixing. For example, mixing by, for example, stirring or sonication.

In the organic solar cell, the matching of donor and acceptor materials is key to achieving efficient energy conversion. This matching is involved in the effectiveness of photo-charge separation and charge transport, as well as the optimization of final cell performance. Firstly, the energy level structures of the donor and acceptor need to be matched in order to facilitate the separation of electrons and holes after photoexcitation. Secondly, the molecular structures of the donor and acceptor materials and the degree of electron cloud delocalization also need to be matched to facilitate charge transport. Additionally, there should be some overlap in the absorption spectra of the donor and the acceptor to ensure that the light energy is sufficiently absorbed and to induce charge separation. And, the charge (Formula 2)

In some embodiments, the asymmetric organic photovoltaic acceptor material in the A-D-D'-A type is named as SM1, wherein R is —$CH_3$ and X is F.

In some embodiments, the asymmetric organic photovoltaic acceptor material in the A-D-D'-A type is named as SM2, wherein R is —$CH_3$ and X is Cl.

In some embodiments, the asymmetric organic photovoltaic acceptor material in the A-D-D'-A type is named as SM3, wherein R is 2-ethylhexyl and X is F.

In some embodiments, the asymmetric organic photovoltaic acceptor material in the A-D-D'-A type is named as SM4, wherein R is 2-ethylhexyl and X is Cl.

One of the embodiments of the present disclosure provides a use of the asymmetric organic photovoltaic acceptor material in the A-D-D'-A type, which may be applied to the photoactive layer of the organic solar cell.

The photoactive layer of the organic solar cell is for absorbing light energy and converting it into electrical energy. In some embodiments, the photoactive layer includes the organic photovoltaic acceptor material and a donor material. The donor material receives electrons, and the acceptor material receives photoexcited positive holes. Under light conditions, the charge transfer between the donor and acceptor materials results in the generation of an electric current, which realizes the conversion of light energy to electrical energy.

The photoactive layer may be prepared by blending the organic photovoltaic acceptor material with the polymer donor material. This typically involves dissolving them in a mobility of the donor and acceptor materials should be appropriately matched to ensure that electrons and holes are able to move quickly upon photoexcitation, reducing recombination losses.

In some embodiments, the use of the asymmetric organic photovoltaic acceptor material in the A-D-D'-A type may include: blending the organic photovoltaic acceptor material with the polymer donor material to prepare the photovoltaic layer of a binary or ternary bulk heterojunction organic solar cell.

In some embodiments, the polymer donor material blended with the asymmetric organic photovoltaic acceptor material in the A-D-D'-A type may be poly[(2,6-(4,8-bis(5-(2-ethylhexyl-3-fluoro)thiophen-2-yl)-benzo[1,2-B:4,5-B'] dithiophene])-alt-(5,5-(1',3'-di-2-thiophene-5',7'-bis(2-ethylhexyl) benzo[1',2'-C:4',5'-C'']dithiophene-4,8-dione)] (PM6).

In some embodiments, a mass ratio of the asymmetric organic photovoltaic acceptor material in the A-D-D'-A type to the PM6 is 1.5:1.

In some embodiments, the use of the asymmetric organic photovoltaic acceptor material in the A-D-D'-A type may further includes preparing the photoactive layer of the binary bulk heterojunction organic solar cell with 1-chloronaphthalene (CN) as a solvent additive.

Specifically, 1-chloronaphthalene as a solvent additive was mixed with the polymer donor material as well as the asymmetric organic photovoltaic acceptor material in the A-D-D'-A type in the embodiments of the present disclosure, and was successively annealed by thermal and $CS_2$ steam annealing to realize the preparation of organic solar cell devices based on a simple and efficient small molecule acceptor.

In some embodiments, the organic solar cell device includes a tin indium oxide (ITO) conductive glass, an anode, an anode modification layer, the photoactive layer, a cathode modification layer, a cathode, or the like.

EXAMPLES

The following embodiments are some more specific illustrations of some of the above embodiments. Some of these embodiments may also be replaced or combined with corresponding elements in other embodiments to form new embodiments. The experimental methods in the following embodiments are conventional if not otherwise noted. The experimental materials used in the following embodiments are, if not otherwise specified, obtained by purchase from a conventional biochemical reagent company. The quantitative tests in the following embodiments were set up with three repetitions of the experiment, and the results were averaged. It should be appreciated that the following embodiments are intended to better explain the present invention and are not intended to limit the invention.

Example 1

Synthesis of an organic photovoltaic acceptor material in an A-D-D'-A-type based on alkoxyindenothiophene.

The synthetic route of SM1 is as follows:

-continued

SM1

1.1 Synthesis of Compound 1

To a 250 mL single-necked flask was added 2-bromo-4-methoxybenzoic acid (25.0 g, 108 mmol) and anhydrous methanol (120 mL). Stirring and slowly adding concentrated sulfuric acid (30 mL) dropwise to the single-necked flask at room temperature, the reaction was heated up to 80° C. for 5 h. The reaction was stopped, and after cooling, the reaction solution was poured into 300 mL of water, extracted by dichloromethane, and dried over anhydrous magnesium sulfate.

After extraction by dichloromethane and drying with anhydrous magnesium sulfate, the organic solvent was removed by decompression distillation, and after drying, compound 1 (26.1 g, 98% yield) was obtained as an oily liquid. $^1$H NMR (400 MHz, CDCl$_3$) δ 7.86 (d, J=8.8 Hz, 1H), 7.20 (s, 1H), 6.86 (d, J=8.8 Hz, 1H), 3.90 (s, 3H), 3.85 (s, 3H).

1.2 Synthesis of Compound 2

In a 250 mL single-necked flask, compound 1 (12.2 g, 50.0 mmol), 2-thienoboronic acid pinacol ester (12.1 g, 65 mmol), Pd(dppf)Cl$_2$ (0.300 g, 0.401 mmol), CuI (0.10 g), 30% K$_2$CO$_3$ (30 mL, 65 mmol), ethanol (20 mL), and THF (80 mL) were successively added. Under nitrogen protection, the reaction was carried out at 80° C. for 6 h. Then the temperature was raised to 140° C. After evaporation of the organic solvent, the reaction mixture was cooled, followed by addition of 30% NaOH (30 mL) and 1,4-dioxane (50 mL). The reaction was continued at 120° C. for 3 h. After cooling to room temperature, the reaction solution was poured into a large amount of water, and filtration was conducted to obtain the filtrate. The filtrate was acidified to pH<1 (resulting in precipitation of a large amount of white solids) by adding HCl, followed by precipitation of a large amount of solids. Subsequently, after filtration and drying, Compound 2 (10.7 g, 92% yield) was obtained as an off-white solid. $^1$H NMR (400 MHz, DMSO-D6) δ 12.66 (s, 1H), 7.70 (d, J=8.4 Hz, 1H), 7.58 (d, J=5.2 Hz, 1H), 7.11 (d, J=3.2 Hz, 1H), 7.10-7.08 (t, J=4.4 Hz, 1H), 7.01 (d, J=8.8 Hz, 1H), 6.95 (d, 1H), 3.83 (s, 3H).

1.3 Synthesis of Compound 3

In a 250 mL single-necked flask, compound 2 (4.68 g, 20.0 mmol) was dissolved in DCM (120 mL), placed at 35° C. with stirring, and sequentially DMF (0.02 mL), SOCl$_2$ (11.9 g, 100 mmol) and SnCl$_2$·2H$_2$O (0.450 g, 2.00 mmol) were added, and the reaction was stirred for 1 h. The mixture was poured into water, extracted with DCM, the solvent was removed by rotary evaporation, and the crude product was separated by column chromatography using a mixture of petroleum ether: dichloromethane (1:1.5, v:v) as eluent to obtain compound 3 (2.75 g, 64% yield) as a yellow solid. $^1$H NMR (400 MHz, CDCl$_3$) δ 7.41 (d, J=8.0 Hz, 1H), 7.20 (d, J=4.8 Hz, 1H), 7.12 (d, J=4.8 Hz, 1H), 6.70 (s, 1H), 6.57 (d, J=8.0 Hz, 1H), 3.86 (s, 3H).

1.4 Synthesis of Compound 4

In a 100 mL two-necked flask, compound 3 (2.5 g, 3.9 mmol), hydrazine hydrate (2 mL), and diethylene glycol (40 mL) were added. The mixture was reacted at 120° C. for 1 h under nitrogen protection, then NaOH (1 g, 25 mmol) was added, and the reaction was heated to 190° C. for 2 h. After cooling, it was poured into water and extracted with DCM, and the solvent was removed by rotary evaporation. The brown liquid was dissolved in DMSO (60 mL), followed by the addition of 1-bromohexane (2.57 g, 15.6 mmol) at 80° C. with stirring, and potassium tert-butoxide (1.75 g, 15.6 mmol) was slowly added. The reaction was continued for 12 h. The reaction mixture was poured into water, extracted with dichloromethane, the organic phases were combined and dried with anhydrous magnesium sulfate. The organic solvent was removed by distillation under reduced pressure and separated by column chromatography using a mixture of petroleum ether: dichloromethane (8:1, v: v) as eluent to give compound 4 (3.2 g, 75% yield) as a slightly yellow oily liquid. $^1$H NMR (400 MHz, CDCl$_3$) δ 7.28 (d, J=4.8 Hz, 1H), 7.14 (d, J=8.0 Hz, 1H), 6.95 (s, 1H), 6.94 (d, J=4.8 Hz, 1H), 6.70 (d, J=8.0 Hz, 1H), 3.85 (s, 3H), 1.94-1.86 (m, 2H), 1.84-1.76 (m, 2H), 1.15-1.08 (m, 16H), 0.80-0.77 (t, J=7.0 Hz, 6H).

1.5 Synthesis of Compound 5

In a 100 mL double-necked flask, compound 4 (3.2 g, 8.65 mmol) and anhydrous tetrahydrofuran (40 mL) were added, and 1.6 M n-butyllithium (8.13 mL, 13.0 mmol) was added slowly and drop wise at −78° C. under nitrogen protection. After 1 h of reaction, DMF (1.14 g, 1.56 mmol) was injected, recovered to room temperature, and the reaction solution was poured into water, acidified with 5 mL of hydrochloric acid, extracted three times with DCM, the organic phases were combined and dried with anhydrous magnesium sulfate. The solvent was removed by rotary distillation and separated by column chromatography using a mixture of petroleum ether: dichloromethane (1:1, v: v) as eluent to afford compound 5 (3.13 g, 91% yield) as a slightly yellow viscous liquid. $^1$H NMR (400 MHz, CDCl$_3$) δ 9.89 (s, 1H), 7.61 (s, 1H), 7.21 (d, J=8.4 Hz, 1H), 7.07 (s, 1H), 6.88 (d, J=8.4 Hz, 1H), 3.88 (s, 3H), 1.99-1.91 (m, 2H), 1.87-1.79 (m, 2H), 1.18-1.08 (m, 16H), 0.81-0.77 (t, J=7.0 Hz, 6H).

1.6 Synthesis of Compound 6a

In a 250 mL double-necked flask, compound 5 (3.10 g, 7.79 mmol) and DCM (100 mL) were added with stirring and dropwise addition of methanesulfonic acid (0.822 g, 8.57 mmol) at room temperature, followed by slow addition of NBS (1.39 g, 7.79 mmol). After 1 h of reaction, the reaction solution was poured into water, extracted with DCM, and the organic phases were combined and dried with K$_2$CO$_3$. The solvent was removed by rotary distillation and separated by column chromatography using petroleum ether: dichloromethane (1:1, v:v) as eluent to give Compound 6a (3.46 g, 93% yield) as a slightly yellow viscous liquid. $^1$H NMR (400 MHz, CDCl$_3$) δ 9.90 (s, 1H), 7.61 (s, 1H), 7.48 (s, 1H), 7.06 (s, 1H), 3.99 (s, 3H), 1.99-1.91 (m, 2H), 1.85-1.77 (m, 2H), 1.18-1.09 (m, 16H), 0.82-0.78 (t, J=7.0 Hz, 6H).

1.7 Synthesis of Compound 7a

In a 100 mL double-necked flask, 4,4-bis(2-ethylhexyl)-dithiophene-cyclopentadiene (1.26 g, 3.00 mmol) and anhydrous tetrahydrofuran (30 mL) were added. Under nitrogen protection, cooled to −78° C. and kept at a constant temperature for 15 min, 1.6 M n-butyl radical (2.16 mL, 3.45 mmol) was added dropwise, and the reaction was stirred for 1 h. After that, 1.0 M trimethyltin chloride (4.00 mL, 4.00 mmol) was added and the reaction was warmed up to 60° C. and continued for 2 h. Compound 6a (0.915 g, 2.3 mmol) and Pd$_2$(dba)$_3$ (30 mg) and P(o-toly)$_3$ (40 mg) were dissolved in toluene (20 mL) and added to the reaction. The reaction was heated to 85° C. and then continued overnight. After cooling to room temperature, the solvent was removed by rotary distillation and separated by column chromatography using petroleum ether: dichloromethane (1:1, v: v) as eluent to give Compound 7a (1.22 g, 66% yield) as an orange-yellow viscous liquid. $^1$H NMR (400 MHz, CDCl$_3$) δ 9.89 (s, 1H), 7.62 (s, 1H), 7.54 (s, 1H), 7.44 (t, J=2.6 Hz, 1H), 7.14 (d, J=4.8 Hz, 2H), 7.13 (s, 1H), 6.95 (m, 1H), 4.04 (s, 3H), 2.01-1.87 (m, 8H), 1.17-1.11 (m, 16H), 1.02-0.91 (m, 18H), 0.84-0.63 (m, 18H).

1.8 Synthesis of Compound 8a

In a 100 mL single-necked flask, DMF (0.912 g, 12.5 mmol) and DCM (30 mL) were added and cooled with an ice-water bath and kept at a constant temperature, and SOCl$_2$ (1.49 g, 12.5 mmol) was added dropwise slowly. After stirring for 1 h, compound 7a (1.00 g, 1.25 mmol) dissolved in 5 mL of DCM was added, and the reaction was stirred at 45° C. for 3 h. After cooling, the reaction was added dropwise to the K$_2$CO$_3$ solution, and 1 mL of triethylamine was added and stirred for 15 min. Extracted with DCM, the organic layer was separated, the solvent was removed by rotary distillation, and the compound was separated by column chromatography using a mixture of petroleum ether: trichloromethane (1:2, v:v) as the eluent, yielding compound 8a (0.522 g, 51% yield) as a red solid. $^1$H NMR (400 MHz, CDCl$_3$) δ 9.91 (s, 1H), 9.83 (s, 1H), 7.64 (s, 1H), 7.58 (t, J=4.0 Hz, 1H), 7.56 (s, 1H) 7.48 (t, J=2.2 Hz, 1H), 7.16 (s, 1H), 4.08 (s, 3H), 2.07-1.94 (m, 8H), 1.17-1.12 (m, 16H), 1.00-0.93 (m, 18H), 0.84-0.63 (m, 18H).

1.9 Synthesis of SM1

In a 50 mL double-necked flask, compound 8a (0.150 g, 0.181 mmol), 5,6-difluoro-1,3-bis(dicyanomethylidene)inden-1-one (0.146 g, 0.634 mmol), THF (20 mL), and pyridine (0.2 mL) were added, and the reaction was stirred at 65° C. for 3 h. Cooled to room temperature, poured into 200 mL of anhydrous methanol for precipitation, then pumped and filtered, and the crude product was extracted using a mixture of petroleum ether: trichloromethane (1:1, v:v) as the eluent, and separated by column chromatography to afford SM1 (0.172 g, 76% yield) as a black solid powder. $^1$H NMR (400 MHz, CDCl$_3$) δ 8.98 (s, 1H), 8.90 (s, 1H), 8.56-8.53 (m, 2H), 7.72-7.64 (m, 4H), 7.64 (s, 1H), 7.57 (s, 1H), 7.30 (s, 1H), 4.12 (s, 3H), 2.07-1.94 (m, 8H), 1.18-1.13 (m, 16H), 1.02-0.95 (m, 18H), 0.81-0.63 (m, 18H).

Example 2

SM2 was prepared with reference to SM1, replacing only the raw material (5,6-difluoro-1,3-bis(dicyanomethylidene)inden-1-one) with 5,6-dichloro-1,3-bis(dicyanomethylidene)inden-1-one.

SM3 and SM4 were prepared with reference to SM1 and SM2, respectively, and the only difference is Compound 6a was replaced with Compound 6b, which is prepared by the following synthetic steps.

2.1 Synthesis of compound 6b

In a 50 mL double-necked flask, Compound 6a (3.20 g, 6.70 mmol) was dissolved in DCM (30 mL) and BBr$_3$ (1 mL) was slowly added dropwise. The reaction mixture was stirred at room temperature for 3 h, then it was poured into 30 mL of saturated aqueous sodium bicarbonate solution and stirring was continued for 10 min. The collected organic phase was dried with Mg$_2$SO$_4$ and then the solution was removed by rotary evaporation. The brown liquid was mixed with K$_2$CO$_3$ (1.85 g, 13.4 mmol), KI (1.11 g, 6.70 mmol), bromo isooctane (2.60 g, 13.4 mmol) and DMF (60 mL), and stirred at 90° C. for 12 h. Cooled to room temperature, poured into 150 mL of water, extracted with DCM, the solvent was removed by evaporation, resulting in a red liquid. The crude product was subjected to column chromatography using a mixture of petroleum ether and dichloromethane (1:1, v:v) as the eluent, yielding Compound 6b (3.46 g, 90%) as a slightly yellow liquid. $^1$H NMR (400 MHz, CDCl$_3$) δ 9.90 (s, 1H), 7.61 (s, 1H), 7.48 (s, 1H), 7.06 (s, 1H), 3.99 (s, 3H), 1.99-1.91 (m, 2H), 1.85-1.77 (m, 2H), 1.18-1.09 (m, 16H), 0.82-0.78 (t, J=7.0 Hz, 6H).

Example 3

Characterization of the Properties of Organic Photovoltaic Acceptor Materials and Preparation and Testing of Photovoltaic Devices:

The $^1$H NMR spectra of all the intermediates and the organic photovoltaic acceptor materials were determined by a Bruker Dex-400 NMR instrument, and UV-visible absorption spectra were determined by a Shimadzu UV-2600 UV-visible spectrophotometer. Cyclic voltammetry curves were tested by a CHI630E electrochemical analyzer, and an acetonitrile solution containing 0.1 M tetrabutylammonium hexafluorophosphate ($Bu_4NPF_6$) was used as the supporting electrolyte.

Organic solar cell devices based on this type of organic photovoltaic acceptor material include a tin-indium oxide (ITO) conductive glass anode, an anode modification layer, a photoactive layer, a cathode modification layer, and a cathode. The photoactive layer material of the organic solar cell includes the organic photovoltaic acceptor material SM4 described in the embodiments of the present disclosure and the commercially purchased polymer donor material PM6, and a mass ratio of the PM6:SM4 blend is 1:1.5. 1-Chloronaphthalene (CN) was added at a ratio of 0.5% of the volume fraction of chloroform solvent (e.g., PM6 is 6 mg, 1-chloronaphthalene is 0.005 mL, and chloroform is 1 mL), and the active layer was successively subjected to 100° C. thermal annealing and $CS_2$ solvent vapor annealing treatments. The binary photovoltaic device can achieve a photovoltaic conversion efficiency of 13.67%.

Figure 1A:
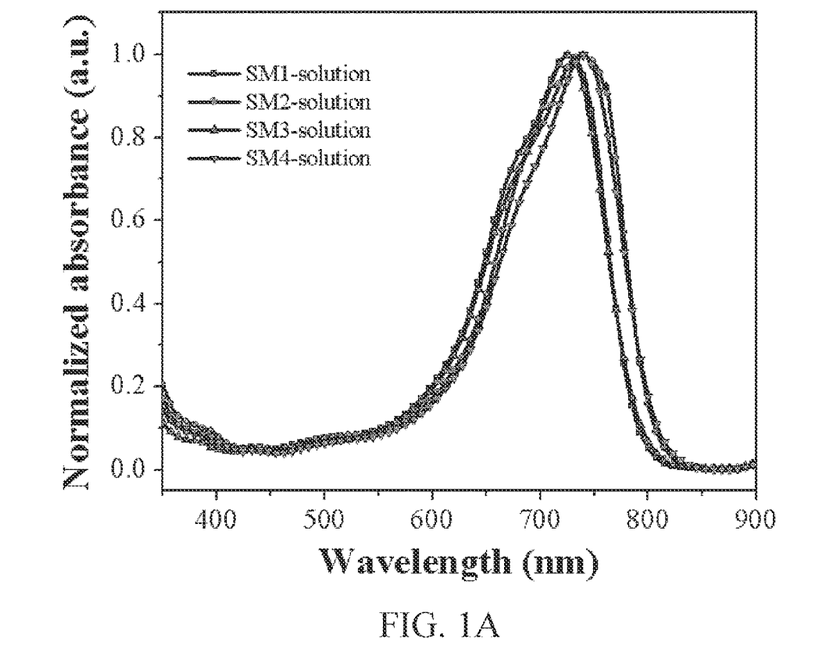
FIG. 1A and FIG. 1B are images illustrating UV-visible absorption spectra of an organic photovoltaic acceptor material according to some embodiments of the present disclosure.
Figure 1B:
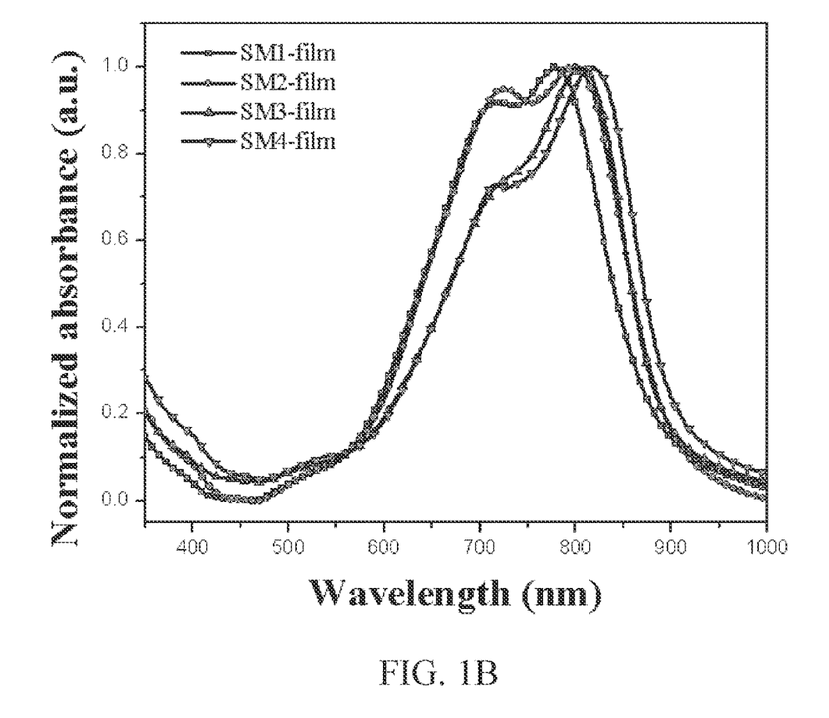

3.1 Determination of Photophysical Properties of Organic Photovoltaic Acceptor Materials FIGS. 1A and 1B illustrate the UV-visible absorption spectra of the organic photovoltaic acceptor materials in chloroform solution and in the film state; as can be seen from FIG. 1A, they have strong absorption in the chloroform solution ($^\varepsilon$=(1.6-2.0)×$10^5$), and their absorption peaks in the solid film are in the 650-900 nm range, which can be attributed to the intramolecular charge transfer (ICT) effect. As shown in FIG. 1B, the films are red-shifted by approximately 100 nm relative to the absorption in the solution. The film of the small-molecule acceptor with methoxyl side chains shows a distinct shoulder peak, while the film of the small-molecule acceptor with iso-octyloxy side chains shows a relative redshift and the absence of a sharp peak, which is due to the enhanced J-aggregation resulting from the bulkier alkyl chains hindering the formation of H-aggregates. The optical band gaps of the organic photovoltaic acceptor materials that can be measured at the same time are 1.38 eV (SM1 and SM3) and 1.35 eV (SM2 and SM4), respectively (the formula is $E_g$=1240/λ, where $E_g$ is the optical band gap and λ is the initial absorption wavelength of the film).

3.2 Electrochemical performance testing of organic small molecule acceptors

Figure 2:
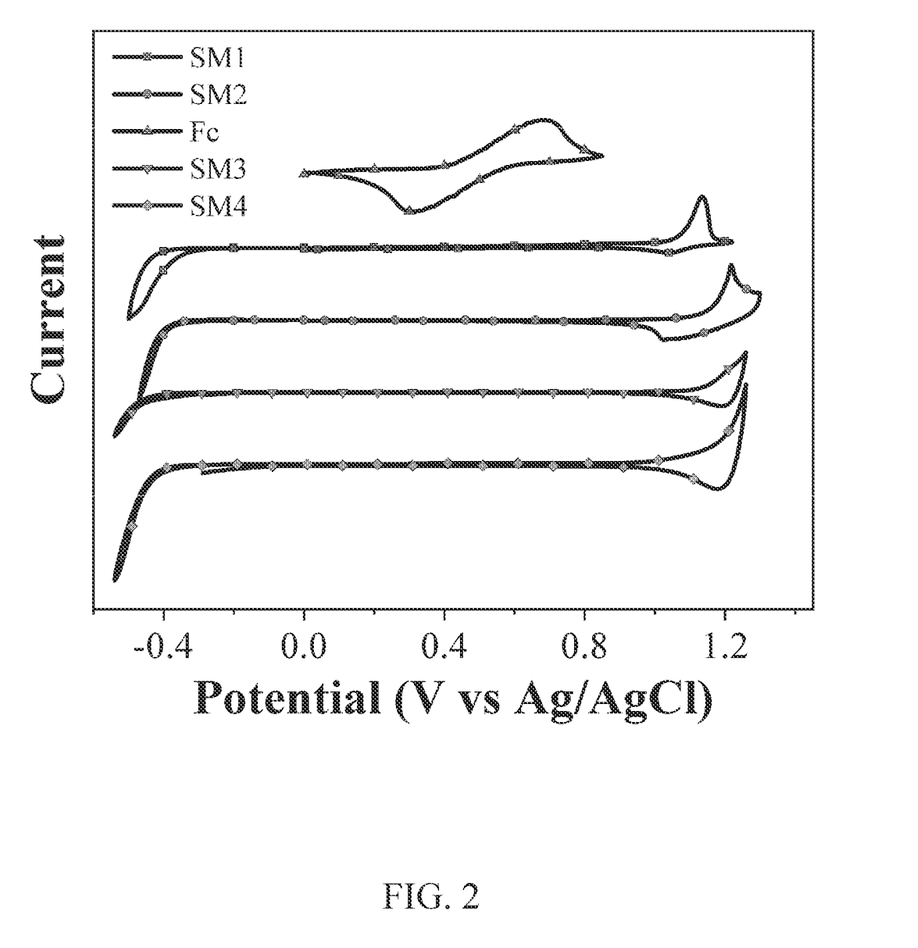
FIG. 2 is a cyclic voltammetry curve illustrating the organic photovoltaic acceptor material according to some embodiments of the present disclosure.

The cyclic voltammogram curves of organic small molecule acceptors SM1, SM2, SM3, and SM4 in solid membranes are shown in FIG. 2. According to the calculation formula $E_{HOMO}$=−($E_{ox}$+4.80) eV, the HOMO energy levels of SM1, SM2, SM3, and SM4 are −5.45 eV, −5.46 eV, −5.47 eV, and −5.49 eV, respectively. According to the formula $E_{LUMO}$=−($E_{red}$+4.80) eV, the LUMO energy levels of SM1, SM2, SM3, and SM4 are derived to be −3.95 eV, −3.96 eV, −4.03 eV, and −4.05 eV, respectively. Thus, the calculated electrochemical band gaps (difference between $E_{HOMO}$ and $E_{LUMO}$) of the organic photovoltaic acceptor materials are 1.50 eV (SM1 and SM2) and 1.44 eV (SM3 and SM4), respectively.

3.3 Photovoltaic Performance Tests of Organic Photovoltaic Acceptor Materials

Figure 3:
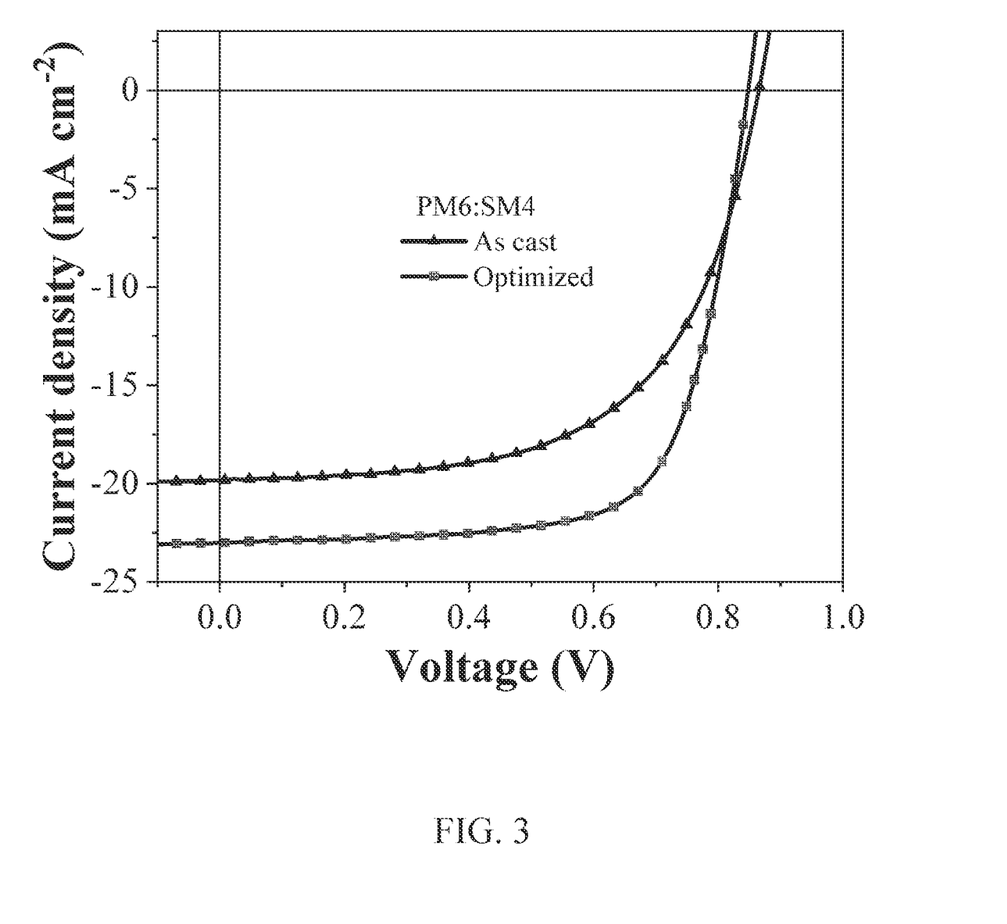
FIG. 3 is a current density-voltage (J-V) plot illustrating the organic solar cell device prepared by mixing PM6 with SM4 according to some embodiments of the present disclosure.

The designed and synthesized SM1 or SM4 were chosen as the acceptor materials, and the commercially purchased polymer PM6 was used as the donor material to prepare positive binary organic solar cell. Under the irradiation of a simulated sunlight source (irradiance of 100 mW/cm$^2$), the J-V curves of the organic solar cell was measured as shown in FIG. 3. The test results show that the short-circuit current ($J_{sc}$) of the organic solar cell device with the device structure of ITO/PEDOT:PSS/PM6:SM1/PFN-Br/Ag is 20.35 mA cm$^2$, open-circuit voltage ($V_{oc}$) of 0.83 V, fill factor (FF) of 70.11%, and PCE of 11.84%; the organic solar cell device with the device structure of ITO/PEDOT:PSS/PM6:SM4/PDIN/Ag has a $J_{sc}$ of 22.99 mA cm-2, a $V_{oc}$ of 0.85 V, a FF of 70.19%, and PCE up to 13.67%.

Figure 4:
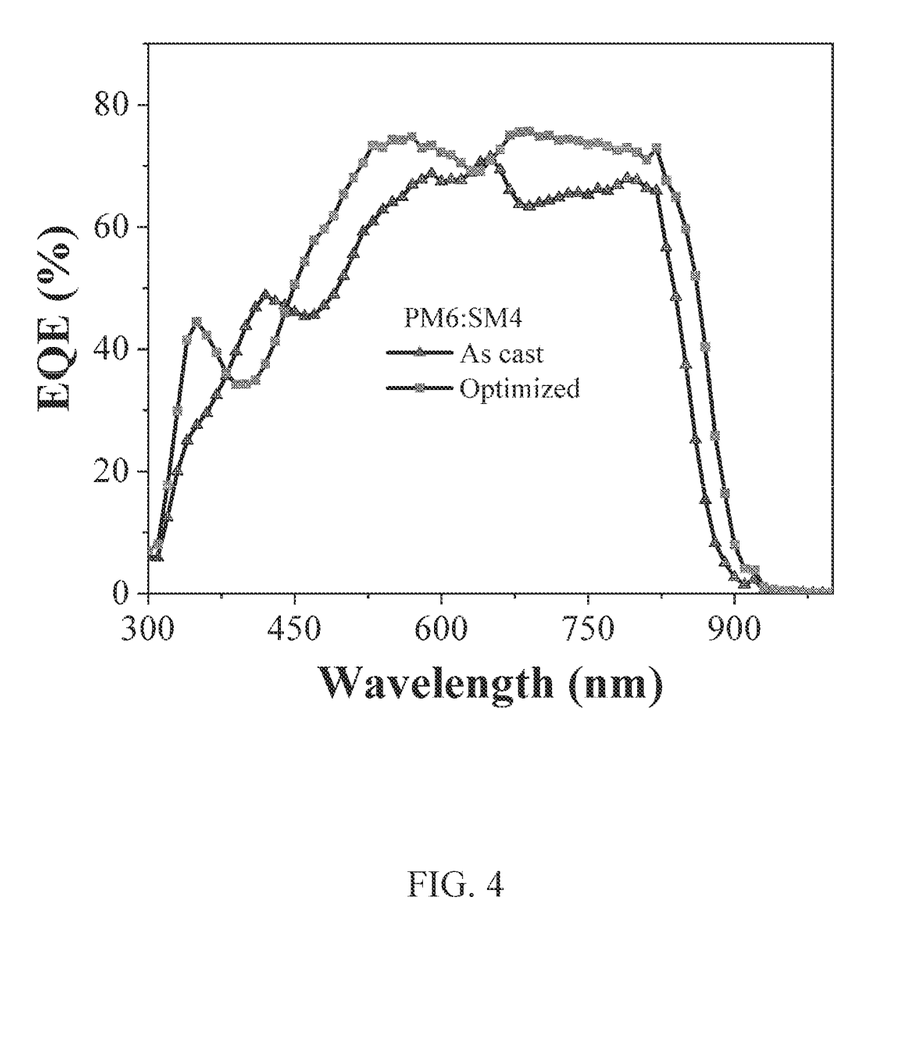
FIG. 4 is a schematic diagram illustrating the external quantum efficiency (EQE) of the organic solar cell device prepared by mixing PM6 with SM4 according to some embodiments of the present disclosure.

The EQE curve of PM6:SM4 is shown in FIG. 4. Under the optimal conditions (PM6:SM4=1:1.5 w/w; chloroform (CF); 1-Chloronaphthalene (CN) accounting for 0.5% volume fraction of chloroform, thermal annealing at 100° C. and steam annealing at $CS_2$), the EQE response of PM6:SM4 was in the range of 300-900 nm, and within the range of 550-850 nm, the EQE reached 70%, with the maximum EQE value at 690 nm being 76%.

The basic concepts have been described above, and it is apparent to those skilled in the art that the foregoing detailed disclosure serves only as an example and does not constitute a limitation of this specification. While not expressly stated herein, various modifications, improvements, and amendments may be made to this specification by those skilled in the art. Such modifications, improvements, and amendments are suggested in this specification and remain within the spirit and scope of the exemplary embodiments of this specification.

Also, the specification uses specific words to describe embodiments of the present disclosure. such as "an embodiment", "one embodiment", and/or "some embodiments" means a feature, structure, or characteristic associated with at least one embodiment of the present disclosure. Accordingly, it should be emphasized and noted that "one embodiment" or "an embodiment" referred to two or more times in different locations in this specification or "a number of embodiments" means a feature, structure, or characteristic related to at least one embodiment of the present disclosure. "an embodiment" or "an alternative embodiment" in different locations in this specification do not necessarily refer to the same embodiment. In addition, certain features, structures, or characteristics in one or more embodiments of the present disclosure may be suitably combined.

Additionally, unless expressly stated in the claims, the order of the processing elements and sequences, the use of numerical letters, or the use of other names as described in this specification are not intended to qualify the order of the processes and methods of the present disclosure. While some embodiments of the invention that are currently considered useful are discussed in the foregoing disclosure by way of various examples, it should be appreciated that such details serve only illustrative purposes, and that additional claims are not limited to the disclosed embodiments, rather, the claims are intended to cover all amendments and equivalent combinations that are consistent with the substance and scope of the embodiments of the present disclosure. For example, although the implementation of various components described above may be embodied in a hardware device, it may also be implemented as a software only solution, e.g., an installation on an existing server or mobile device.

Similarly, it should be noted that in order to simplify the presentation of the disclosure of the present disclosure, and thereby aid in the understanding of one or more embodiments of the invention, the foregoing descriptions of embodiments of the present disclosure sometimes group multiple features together in a single embodiment, accompanying drawings, or a description thereof. However, this method of disclosure does not imply that more features are required for the objects of the present disclosure than are mentioned in the claims. Rather, claimed subject matter may lie in less than all features of a single foregoing disclosed embodiment.

Numbers describing the numbers, attributes, and properties of components are used in some embodiments, and it is to be understood that such numbers used in the description of embodiments are modified in some examples by the modifiers "about", "approximately", or "substantially". ", "approximately", or "generally" is used in some examples. Unless otherwise noted, the terms "about," "approximate," or "approximately" indicate that a ±20% variation in the stated number is allowed. Correspondingly, in some embodiments, the numerical parameters used in the specification and claims are approximations, which are subject to change depending on the desired characteristics of individual embodiments. In some embodiments, the numerical parameters should take into account the specified number of valid digits and use a general digit retention method. While the numerical domains and parameters used to confirm the breadth of their ranges in some embodiments of the present disclosure are approximations, in specific embodiments such values are set to be as precise as possible within a feasible range.

For each patent, patent application, patent publication application, and other material cited in the present disclosure, such as articles, books, specification sheets, publications, documents, etc., the entire contents of which are hereby incorporated herein by reference. Excluded are application history documents that are inconsistent with or create a conflict with the contents of the present disclosure, as well as documents that limit the broadest scope of the claims of the present disclosure (currently or hereafter appended to the present disclosure). It should be noted that in the event of any inconsistency or conflict between the descriptions, definitions, and/or use of terminology in the materials appended to the present disclosure and those set forth herein, the descriptions, definitions and/or use of terminology in the present disclosure prevail.

Finally, it should be understood that the embodiments described in the present disclosure are only used to illustrate the principles of the embodiments of the present disclosure. Other deformations may also fall within the scope of the present disclosure. As such, alternative configurations of embodiments of the present disclosure may be viewed as consistent with the teachings of the present disclosure as an example, not as a limitation. Correspondingly, the embodiments of the present disclosure are not limited to the embodiments expressly presented and described herein.

What is claimed is:

1. An asymmetric organic photovoltaic acceptor material in an A-D-D'-A type, wherein the asymmetric organic photovoltaic acceptor material has a structure represented by Formula 1:

wherein $R^1$, $R^2$, $R^3$ are linear or branched $C_{1-20}$ alkyl; and X is an H, F or Cl atom.

2. The asymmetric organic photovoltaic acceptor material in the A-D-D'-A type according to claim 1, wherein the asymmetric organic photovoltaic acceptor material has a structure represented by Formula 2:

(Formula 2)

wherein
- when R is —CH3 and X is F, the asymmetric organic photovoltaic acceptor material is named as SM1;
- when R is —CH3 and X is Cl, the asymmetric organic photovoltaic acceptor material is named as SM2;
- when R is 2-ethylhexyl and X is F, the asymmetric organic photovoltaic acceptor material is named as SM3; or
- when R is 2-ethylhexyl and X is Cl, the asymmetric organic photovoltaic acceptor material is named as SM4.

3. A use of the asymmetric organic photovoltaic acceptor material in the A-D-D'-A type according to claim 1, wherein the asymmetric organic photovoltaic acceptor material is applied to a photoactive layer of an organic solar cell.

4. The use of the asymmetric organic photovoltaic acceptor material in the A-D-D'-A type according to claim 3, wherein the asymmetric organic photovoltaic acceptor material is blended with a polymer donor material to prepare a photoactive layer of a binary or ternary bulk heterojunction organic solar cell.

5. The use of the asymmetric organic photovoltaic acceptor material in the A-D-D'-A type according to claim 4, wherein the polymer donor material is PM6, and a mass ratio of the asymmetric organic photovoltaic acceptor material to the PM6 is 1:1.5.

6. The use of the asymmetric organic photovoltaic acceptor material in the A-D-D'-A type according to claim 4, wherein the photoactive layer of the binary bulk heterojunction organic solar cell is prepared by using 1-chloronaphthalene as a solvent additive.

* * * * *